United States Patent [19]

Kudzma et al.

[11] Patent Number: 4,801,615
[45] Date of Patent: Jan. 31, 1989

[54] 4-HETEROHEXACYCLIC-4-(N-(PHENYL-)AMIDO) PIPERIDINE DERIVATIVES AND PHARMACEUTICAL COMPOSITIONS AND METHOD EMPLOYING SUCH COMPOUNDS

[75] Inventors: Linas V. Kudzma, North Bergen; H. Kenneth Spencer, Chatham, both of N.J.

[73] Assignee: The BOC Group, Inc., Montvale, N.J.

[21] Appl. No.: 139,895

[22] Filed: Dec. 31, 1987

[51] Int. Cl.$^4$ .................. A61K 31/44; C07D 211/68
[52] U.S. Cl. ...................................... 514/318; 546/193; 546/194
[58] Field of Search ................. 546/193, 194; 514/318

[56] References Cited

U.S. PATENT DOCUMENTS 3,164,600  1/1965  Janssen ............................. 546/193
3,998,834  12/1976  Janssen et al. ..................... 546/193
4,584,303  4/1986  Huang et al. ...................... 514/326
4,675,326  6/1987  Amitai et al. ..................... 546/193

OTHER PUBLICATIONS

McElvain, et al., "Piperidine Derivatives", (1958) JACS, vol. 80 pp. 3915–3923.

*Primary Examiner*—Mary C. Lee
*Assistant Examiner*—Robert C. Whittenbaugh

[57] ABSTRACT

Compounds are disclosed of the formula

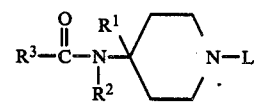

where $R^1$ is a six numbered heterocyclic ring; $R^2$ is a substituted or unsubstituted phenyl; $R^3$ is lower alkyl, and L is selected from a variety of groups.

15 Claims, No Drawings

4-HETEROHEXACYCLIC-4-(N-(PHENYL)AMIDO) PIPERIDINE DERIVATIVES AND PHARMACEUTICAL COMPOSITIONS AND METHOD EMPLOYING SUCH COMPOUNDS

BACKGROUND OF THE INVENTION

The present invention relates to 4-heterocyclic-4-[N-(phenyl)amido]piperidine derivatives and methods and compositions employing such compounds. In particular, this new class of compounds has been found to possess desirable analgesic and anesthetic properties.

A number of patents disclose certain N-phenyl-N-(4-piperidinyl)amides having analgesic activity. For example, some such compounds are disclosed in U.S. Pat. Nos. 3,164,600 and 3,998,834. U.S. Pat. No. 3,164,600 discloses such compounds in which the 4 position of the piperidine ring is substituted by a lower alkyl.

According to the report of S. McElvain et al., JACS, Vol. 80 (1958), changes in the 4-position of certain substituted piperidines generally lead to less or no analgesic activity. For example, McElvain et al. teaches that in going from methyl to butyl, there is no apparent effect on the degree of analgesia, and the 4-phenyl substituent fails to produce any marked effect.

SUMMARY OF THE INVENTION

Compounds of the present invention possess potent analgesic and anesthetic properties. The preferred compounds of the present invention when administered to mammals allow rapid recovery including early regain for muscle coordination. Respiratory depression during use is relatively low compared to commonly known intravenous anesthetics such as fentanyl. Heart rate decrease and arterial pressure decrease are also less. The present compounds are therefore safer, especially for coronary patients.

It has now been found that very desirable against properties are provided by compounds of the formula:

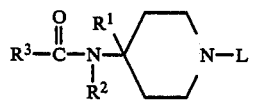
(I)

optically active isoermic forms thereof, and/or pharmaceutically acceptable acid addition salts thereof. In the Formula (I) above, $R^1$ is pyridyl; $R_2$ is substituted or unsubstituted phenyl wherein the substituent is a halogen atom; $R^3$ is a lower alkyl; and L may be a variety of groups including phenyl lower alkyl; (4,5-di-hydro-5-oxo-1H-tetrazol-1-yl) lower alkyl which can be substituted in the 4-position with a lower alkyl group; and pyrazolyl lower alkyl.

A preferred class of compounds within the scope of the present invention are of the formula

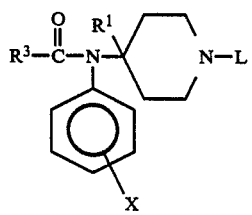

optically active isomeric forms thereof, and/or pharmaceutically acceptable acid addition salts thereof, in which formula: $R^1$ is pyridyl; X is a hydrogen or fluoro group; $R^3$ is a lower alkyl of 1 to 4 carbon atoms; and L is phenyl lower alkyl, pyrazolyl lower alkyl or 4,5-dihydro-5-oxo-1H-tetrazol-1-yl substituted in the 4-position with a lower alkyl.

DETAILED DESCRIPTION OF THE INVENTION

As noted above, the compounds of the invention have the formula

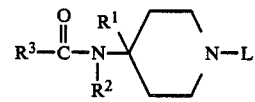

wherein $R^1$ is pyridyl; $R^2$ is substituted or unsubstituted phenyl; $R^3$ is a lower alkyl; and L is phenyl lower alkyl, pyrazolyl lower alkyl; and (4,5-di-hydro-5-oxo-1H-tetrazolyl) lower alkyl which can be substituted in the 4-position with a lower alkyl group. The compounds can be in the form of pharmaceutically acceptable acid addition salts, optically active isomers, and/or cis/trans isomers thereof.

A preferred $R^1$ group is 2-pyridyl.

Preferred $R^2$ groups are phenyl 2-fluorophenyl.

The group $R^3$ in Formula I above is a lower alkyl. Examples of suitable $R^3$ groups include methyl, ethyl, propyl, butyl, pentyl, or hexyl. Preferred $R^3$ groups are methyl and ethyl.

Suitable L groups include 2-phenylethyl, 1-phenyl-2-propyl, and 2-phenyl-1-propyl, 2-(4-ethyl-4,5-di-hydro-5-oxo-1H-tetrazol-1-yl)ethyl, and 2-(1H-pyrazol-1-yl)ethyl.

By lower-alkyl or lower alkoxy groups, we mean branched or unbranched groups containing from 1 to 6 carbon atoms and preferably 1 to 4 carbon atoms.

The compounds of the invention can exist in the form of the free base or the therapeutically or pharmaceutically acceptable acid addition salts by treatment with an appropriate acid, such as an inorganic acid, e.g., hydrochloric, hydrobromic, sulfuric, nitric, phosphoric acids and the like; or an organic acid such as acetic, trifluoroacetic, propionic, hydroxyacetic, methoxyacetic, benzoic, citric, oxalic, methanesulfonic, ethanesulfonic, benzenesulfonic, toluenesulfonic, succinic, tartaric, and the like acids. Preferred acid addition salts are the chloride and oxalate or citrate. These acid addition salts can be prepared by conventional methods, e.g., by treatment with the appropriate acid.

Compounds of the invention having at least one asymmetric carbon atom can exist in optically active isomeric forms. For example, in compounds in which L is 1-phenyl-2-propyl group, the carbon adjacent to the piperidinyl nitrogen is an assymetric carbon and such compounds can therefore exist in optical active isomeric (enantiomeric) forms. Such isomeric forms can be isolated from the racemic mixtures by techniques known those skilled in the art.

The compounds of the invention, prepared as the free base, can be combined with a pharmaceutically acceptable carrier to provide a pharmaceutical composition. Suitable carriers of the free bases include propylene glycol-alcohol-water, isotonic water, sterile water for injection, USP, emulphor TM-alcohol-water, cremphor-EL ™ or other carriers known to those skilled in the art.

The compounds of the invention prepared as the pharmaceutically acceptable acid addition salts can also be combined with a pharmaceutically acceptable carrier to provide a pharmaceutical composition. Suitable carriers for the acid addition salts may include an isotonic aqueous solution, or sterile water for injection, USP, alone or in combination with other solubilizing agents such as ethanol, propylene glycol, or other conventional solubilizing agents known to those skilled in the art. Of course, the carrier will vary depending upon the mode of administration desired for the pharmaceutical composition as is conventional in the art. A preferred carrier is an isotonic aqueous solution containing from 0.0001 mg/ml to 0.5 mg/ml of at least one of the compounds of this invention depending upon the pharmacology of the individual compounds being employed in the formulation.

The compounds of the invention can be administered to mammals, e.g., animals or humans, in amounts effective to provide the desired therapeutic effect. The compounds can be administered intravenously, intramuscularly or subcutaneously in the previously described carriers. These compounds may also be administered orally, sublingually, rectally, or transcutaneously with a suitable pharmaceutically acceptable carrier for that mode of administration as is conventional in the art.

As noted above, an effective amount of the compounds of the present invention is employed to obtain the desired therapeutic effect. Since the activity of the compounds and the depth of the desired therapeutic effect vary, the dosage level employed of the compound also varies. The actual dosage administered will be determined by such generally recognized factors as the body weight of the patient or the idiosyncrasies of the particular patient. Thus, the unit dosage for a particular patient (man) can be as low as (0.00005 mg/Kg,) which the practitioner may titrate to the desired effect.

The compounds of the present invention can be prepared beginning with known piperidones as shown below:

For example, the compound 1-phenylethyl-4-piperidone can be prepared according to the procedure published by A. H. Becket, A. F. Casey and G. Kirk, *J. Med. Pharm. Chem.*, Vol. 1, 37 (1959). The compound 1-benzyl-4-piperidone can be prepared in an analogous manner by the procedures described by C. R. Ganellin and R. G. Spickch, *J. Med. Chem.*, Vol. 8, 619 (1965) or P. M. Carabateas and L. Grumbach, *J. Med. Pharm. Chem.*, Vol. 5, 913 (1962). Compounds with other L groups can be prepared as disclosed in U.S. Pat. No. 4,584,303 and Ser. No. 009,857 filed on Feb. 2, 1987, both incorporated herein by reference.

In one example of a process of the invention, L-piperidone may be reacted with phenyl amine and the resulting Schiff base may be further reacted with, for example, a heterocyclic lithium agent to give a 4-heterocyclic-aminopiperidine or the corresponding substituted heterocyclic compound if a substituted heterocyclic amine is used. The following reaction scheme, wherein $R^1$ represents a heterocyclic group according to the present invention, illustrates such a method:

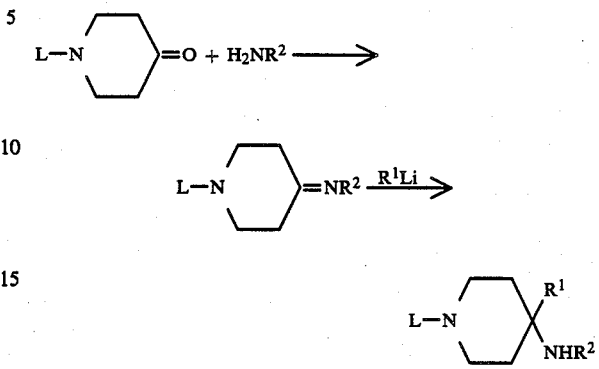

The latter compound can be reacted with the appropriate acid halide, e.g. $R^3(COCl)$ or anhydride $(R^3CO)_2O$ to introduce the appropriate $R^3$—CO— group onto the amino nitrogen as follows.

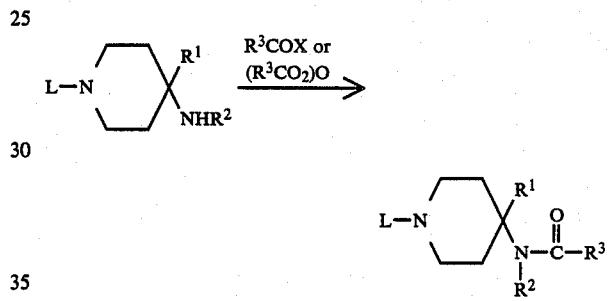

L may originally be phenylmethyl and when L is not phenylmethyl in the final product, one procedure for preparing compounds of the present invention is to subsequently split off the benzyl group and replace it with the desired L group. For example, the compounds of the invention may be prepared when starting with 1-benzyl-4-piperidone by the following reaction scheme:

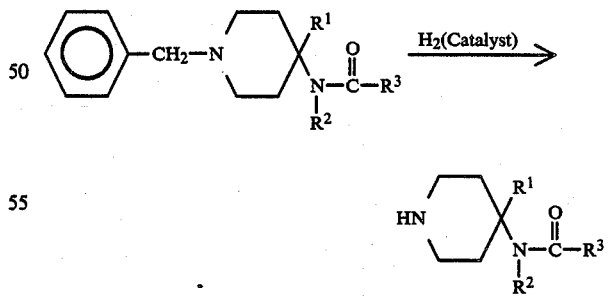

An alternative method of replacing the L group involves employing alpha-chloro-ethylchloroformate followed by methanolysis to accomplish debenzylation.

The appropriate L group can then be introduced by reacting the latter compound with an appropriately reactive molecule LX wherein X is, for example, halogen such as chlorine, bromine or iodine, e.g., as illustrated below

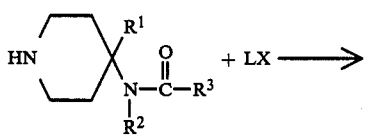

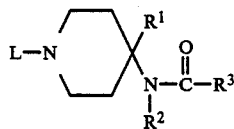

The reaction of LX can be conducted in an inert organic solvent such as, for example, N,N-dimethylformamide (DMF) or acetonitrile in the presence of an appropriate base such as alkali metal carbonate.

Compounds of the invention may also be prepared via a nitrile intermediate by the following reaction scheme:

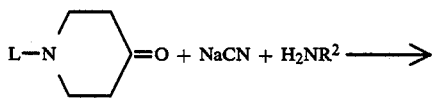

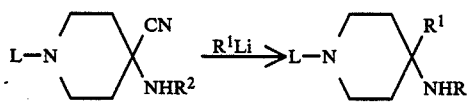

The remaining steps may proceed as shown above.

The following examples are presented fro the purposes of demonstrating, but not limiting the compounds or compositions of this invention.

EXAMPLE 1

In a well ventilated hood a solution of potassium cyanide (110.5 gms, 1.69 mol) in 680 mls of deionized water was stirred at room temperature ("RT"). To this solution was added aniline (157.6 gms, 1.69 mol) in 320 mls of methanol. The resulting solution was cooled in an ice/water bath and 12N HCl (140 mls, 1.68 mol) was added dropwise with cooling (Caution HCN). N-benzyl-4-piperidone (320 gms, 1.69 mol) was slowly added with cooling followed by warming reaction mixture to RT. The reaction mixture was stirred at RT for 8 days. When stirring was stopped the reaction mixture separated to two layers. The top aqueous methanol layer was decanted to leave a gummy solid. 200 mls of isopropanol was added to the gummy residue and the mixture was vigorously stirred for 45 minutes. A finely divided solid was formed. This solid was filtered, washed with isopropanol and dried in an over (50° C.) to give 288.2 gms (58.5%) of the desired alpha-amino nitrile as a white powder.

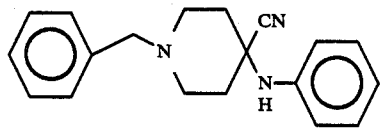

EXAMPLE 2

2-Bromopyridine (11.17 gms, 70.6 mmol) was added dropwise to a cold (−78° C.) solution of butyllithium (60.8 mmol) in 150 mls anhydrous 3:2 THF/hexane under argon. The now dark orange solution was stirred at −78° C. for 10 min. followed by the addition, via cannula, of the nitrile (8.79 gms, 30.16 mmol) prepared in Example 1 as a solution in 50 mls of anhydrous THF. The reaction mixture turned dark brown and was stirred at −78° C. for 5 min. followed warming to RT. The reaction mixture was quenched by slow dropwise addition of 20 mls of water with cooling in water/ice bath. The reaction mixture was concentrated in vacuo and the residue was extracted with toluene. The toluene layer was separated, dried (Na₂SO₄) and concentrated to give the crude amine as a dark brown oil. The oil was purified by flash chromatography on silica 60 (230–400 mesh) eluting with 1:1 EtOAc/hexane to give 5.2 gms of pure amine (50.2%).

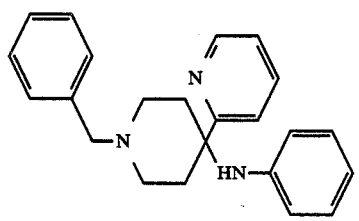

1-benzyl-4-(2-pyridyl)-4-(N-phenyl)piperidine
NMR: 8.65 (d, 1H), 7.90–6.20 (m, 13H), 4.20 (br s, 1H), 3.50 (s, 2H), 2.90–1.80 (m, 8H).
mp=107° C.

EXAMPLE 3

The amine (4.5 gms, 13.1 mmol) of Example 2 was dissolved in 50 mls of propionic anhydride and heated at reflux for 18 hrs. The reaction was then cooled to RT and the propionic anhydride was removed in vacuo. The residue was taken up in 150 mls of toluene and stirred with 200 mls 10% aqueous NaOH for 1 hr. The organic layer was separated, dried over Na₂SO₄ and concentrated to give a black oil. This crude oil was purified by flash chromatography on silica 60 (230–400 mesh) eluting with 1:1 EtOAc/hexane to give amide as a tan oil (2.57 gms, 49%).

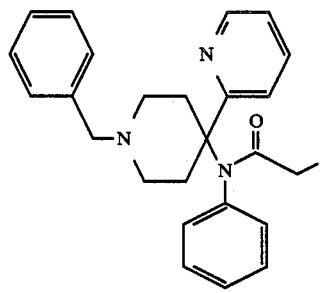

1-benzyl-4-(2-pyridyl)-4-(N-phenylpropionamido)-piperidine
%CHN Analysis of oxalate salt

| Calc. | % C(68.69) | % H(6.38) | % N(8.58) |
|---|---|---|---|
| Found | 68.46 | 6.35 | 8.33 |

NMR: 8.60 (d, 1H), 7.90–6.50 (m, 13H), 3.35 (s, 2H), 3.00–0.90 (complex, 10H), 0.70 (t, 3H)

EXAMPLE 4

The amide (1.96 gms, mmol) of Example 3 was dissolved in 50 mls of methanol and 2 gms of 20%Pd(OH)$_2$ on activated carbon (Pearl-man's catalyst) was added. The solution was shaken on a Parr hydrogenerator at 50 psi H$_2$ for 4 hrs with heating (40° C.). The reaction was then cooled, filtered and concentrated in vacuo to give nor-compound as a pale yellow oil (1.39 gms, 92%).

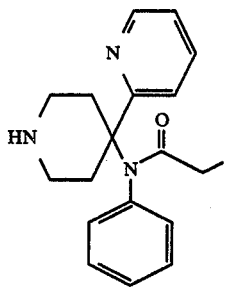

EXAMPLE 5

The nor-compound (695 mg, 2.25 mmol) of Example 4 was dissolved in 50 mls of acetonitrile. The solution was stirred and K$_2$CO$_3$ (1.5 gms) and phenylethyl bromide (600 mgs, 3.24 mmol) were added. The reaction was heated at reflux for 2 days after which the reaction was cooled, filtered and concentrated in vacuo. The residue was chromatographed on silica 60 (230–400 mesh) eluting with 1:1 ethyl acetate/hexanes to give the desired product sa a solidifying oil (513 mg, 55%).
1-(2-phenylethyl)-4-(2-pyridyl)-4-(N-phenylpropionamido)piperidine
%CHN Analysis of oxalate salt
mp=193°–94° C.

| Calc. | % C(69.19) | % H(6.60) | % N(8.34) |
|---|---|---|---|
| Found | 69.16 | 6.84 | 8.43 |

NMR: 8.70 (d, 1H), 8.00–6.90 (m, 13H), 3.20–1.55 (complex, 14H) 1.85 (t, 3H)

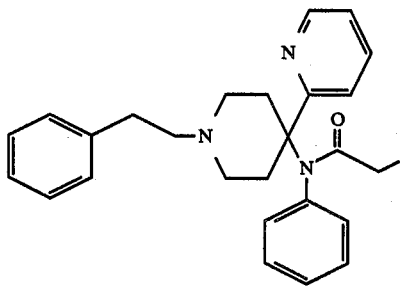

The ED$_{50}$ values were obtained from the mouse hot plate analgesia test (58° C.) described in Domer, Floyd R., *Animal Experiments in Pharmacological Analysis,* Charles C. Thomas, Springfield, 1971, p. 283 ff. The compounds listed in Table 1 below were tested by this procedure and found to have the analgesic activites listed in Table 1.

TABLE

| | Compound | M.P. °C. | Analgesic Activity (ED$_{50}$) mg/Kg Mice |
|---|---|---|---|
| 1. | 1-(2-phenylethyl)-4-(2-pyridyl)-4-(N—phenyl-propionamido] piperidinium oxalate | 193–194 | 0.013 |
| 2. | 1-(2-phenylethyl)-4-(2-pyridyl)4-[N—(2-fluorophenyl)propionamido] piperidinium oxalate | 216 | 0.01 |
| 3. | 1-[2-(4-ethyl-4,5-dihydro-5-oxo-1H—tetrazol-1-yl)ethyl]-4-(2-pyridyl)-4-(N—phenyl propionamido) piperidinium oxalate | 166–67 | 0.438 |
| 4. | 1-[2-(4-ethyl-4,5-dihydro-5-oxo-1H—tetrazol-1-yl)ethyl]-4-(2-pyridyl)-4-[N—(2-fluorophenyl)propionamido] piperidinium oxalate | 180–81.5 | 0.115 |
| 5. | 1-[2-(1H—pyrazol-1-yl)ethyl]-4-(2-pyridyl)-4-[N—(2-fluorophenyl)propionamido] piperidinium oxalate | 180–82 | 0.059 |
| 6. | 1-[2-(1H—pyrazol-1-yl)ethyl]-4-(2-pyridyl)-4-(N—phenylpropionamido)piperidinium oxalate | 183–84 | 0.167 |

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound of the formula

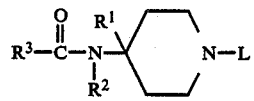

optically active isomeric forms thereof, or a pharmaceutically acceptable salt thereof, in which formula: R$^1$ is 2-pyridyl; R$^2$ is substituted or unsubstituted phenyl wherein the substituent is a halogen atom; R$^3$ is a lower alkyl; and L is phenyl lower alkyl; pyrazolyl lower alkyl; or (4,5-di-hydro-5-oxo-1H-tetrazolyl) lower alkyl which is unsubstituted or substituted in the 4-position with a lower alkyl.

2. A compound according to claim 1, which consists of 1-(2-phenylethyl)-4-(2-pyridyl)-4-(N-phenyl-propionamido)piperidine or salt thereof.

3. A compound according to claim 1, which consists of 1-(2-phenylethyl)-4-(2-pyridyl)4-[N-(2-fluorophenyl)propionamido]piperidine or salt thereof.

4. A compound according to claim 1, which consists of 1-[2-(4-ethyl-4,5-dihydro-5-oxo-1H-tetrazol-1-yl)ethyl]-4-(2-pyridyl)-4-(N-phenylpropionamido)piperidine or salt thereof.

5. A compound according to claim 1, which consists of 1-[2-(4-ethyl-4,5-dihydro-5-oxo-1H-tetrazol-1-yl)ethyl]-4-(2-pyridyl)-4-[N-(2-fluorophenyl)propionamido]piperidine or salt thereof.

6. A compound according to claim 1, which consists of 1-[2-(1H-pyrazol-1-yl)ethyl]-4-(2-pyridyl)-4-[N-(2-fluorophenyl)propionamido]piperidine or salt thereof.

7. A compound according to claim 1, which consists of 1-[2-(1H-pyrazol-1-yl)ethyl]-4-(2-pyridyl)-4-(N-phenylpropionamido)piperidine or salt thereof.

8. A narcotic antagonist or analgesic composition comprising a non-toxic pharmaceutically acceptable carrier and therapeutically effective amount of a compound of the formula

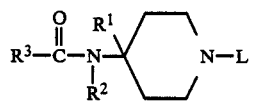

optically active isomeric forms thereof, or a pharmaceutically acceptable salt thereof, in which formula: $R^1$ is 2-pyridyl; $R^2$ is substituted or unsubstituted phenyl wherein the substituent is a halogen atom; $R^3$ is a lower alkyl; and L is phenyl lower alkyl; pyrazolyl lower alkyl; or (4,5-di-hydro-5-oxo-1H-tetrazolyl) lower alkyl which is unsubstituted or substituted in the 4-position with a lower alkyl.

9. A composition according to claim 8, which consists of 1-(2-phenylethyl)-4-(2-pyridyl)-4-(N-phenylpropionamido)piperidine or salt thereof.

10. A composition according to claim 8, which consists of 1-(2-phenylethyl)-4-(2-pyridyl)4-[N-(2-fluorophenyl)propionamido]piperidine or salt thereof.

11. A composition according to claim 8, which consists of 1-[2-(4-ethyl-4,5-dihydro-5-oxo-1H-tetrazol-1-yl)ethyl]-4-(2-pyridyl)-4-(N-phenylpropionamido)-piperidine or salt thereof.

12. A composition according to claim 8, which consists of 1-[2-(4-ethyl-4,5-dihydro-5-oxo-1H-tetrazol-1yl)ethyl]-4-(2-pyridyl)-4-[N-(2-fluorophenyl)propionamido]piperidine or salt thereof.

13. A composition according to claim 8, which consists of 1-[2-(1H-pyrazol-1-yl)ethyl]-4-(2-pyridyl)-4-[N-(2-fluorophenyl)propionamido]piperidine or salt thereof.

14. A composition according to claim 8, which consists of 1-[2-(1H-pyrazol-1-yl)ethyl]-4-(2-pyridyl)-4-(N-phenylpropionamido)piperidine or salt thereof.

15. A method for providing analgesia in a mammal, comprising administering to such mammal an analgesically effective amount of a compound of the formula

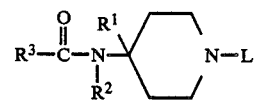

optically isomeric forms thereof, or a pharmaceutically acceptable salt thereof, in which formula: $R^1$ is 2-pyridyl; $R^2$ is substituted or unsubstituted phenyl wherein the substituent is a halogen atom; $R^3$ is a lower alkyl; and L is phenyl lower alkyl; pyrazolyl; lower alkyl or (4,5-di-hydro-5-oxo-1H-tetrazol-1-yl) lower alkyl which is unsubstituted or substituted in the 4-position with a lower alkyl.

* * * * *